US009428724B2

(12) United States Patent
Fricking

(10) Patent No.: US 9,428,724 B2
(45) Date of Patent: Aug. 30, 2016

(54) BIOREACTOR WITH FEED AND HARVEST FLOW THROUGH FILTER ASSEMBLY

(75) Inventor: Patric Fricking, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 338 days.

(21) Appl. No.: 13/984,937

(22) PCT Filed: Feb. 22, 2012

(86) PCT No.: PCT/SE2012/050198
§ 371 (c)(1),
(2), (4) Date: Aug. 12, 2013

(87) PCT Pub. No.: WO2012/115586
PCT Pub. Date: Aug. 30, 2012

(65) Prior Publication Data
US 2013/0316396 A1 Nov. 28, 2013

(30) Foreign Application Priority Data
Feb. 24, 2011 (SE) ........................ 1150158

(51) Int. Cl.
C12M 1/12 (2006.01)
C12M 1/00 (2006.01)
C12M 3/06 (2006.01)
C12M 1/26 (2006.01)

(52) U.S. Cl.
CPC ............ C12M 33/14 (2013.01); C12M 1/12 (2013.01); C12M 3/06 (2013.01); C12M 3/067 (2013.01); C12M 21/00 (2013.01); C12M 27/16 (2013.01); C12M 29/04 (2013.01); C12M 29/10 (2013.01)

(58) Field of Classification Search
CPC ...... C12M 27/16; C12M 33/14; C12M 3/06; C12M 3/067; C12M 1/12; C12M 21/00; C12M 29/04; C12M 29/10
See application file for complete search history.

(56) References Cited

U.S. PATENT DOCUMENTS

| 5,032,524 A | 7/1991 | Buntemeyer et al. |
| 5,688,687 A * | 11/1997 | Palsson .................. C12M 23/42 435/293.2 |
| 6,544,788 B2 | 4/2003 | Singh |

(Continued)

FOREIGN PATENT DOCUMENTS

| CN | 101336290 | 12/2008 |
| CN | 101971001 | 2/2011 |

(Continued)

OTHER PUBLICATIONS

Search Report and Office Action Dated Jun. 23, 2014 Issued on Corresponding Chinese Patent Application No. 201280010213.1.

Primary Examiner — John Kim
(74) Attorney, Agent, or Firm — Wood IP LLC

(57) ABSTRACT

The present invention relates to a bioreactor and a method for operating a bioreactor which comprises a chamber (100) capable of receiving a liquid media, and a filter assembly (200) comprising a perfusion filter (210; 212; 214). The filter assembly (200) is disposed in the chamber (100) and the filter assembly (200) is free to move within the chamber (100). The filter assembly (200) comprises means for coupling a harvesting flow through said filter (210; 212; 214) and means for coupling a feed flow through said filter in an opposite direction compared to the harvesting flow. Through this arrangement, the clogging prevention of the perfusion filter can be improved.

10 Claims, 3 Drawing Sheets

(56) References Cited

U.S. PATENT DOCUMENTS

| | | | |
|---|---|---|---|
| 9,017,997 B2 * | 4/2015 | Wuenn | C12M 23/14 435/297.1 |
| 2003/0036192 A1 | 2/2003 | Singh | |
| 2004/0110273 A1 | 6/2004 | Akers et al. | |
| 2011/0020922 A1 | 1/2011 | Wuenn et al. | |

FOREIGN PATENT DOCUMENTS

| | | |
|---|---|---|
| FR | 2679248 | 1/1993 |
| JP | 2009142182 | 7/2009 |
| WO | WO 2007/076865 | 7/2007 |
| WO | WO 2011/005773 | 1/2011 |

* cited by examiner

US 9,428,724 B2

BIOREACTOR WITH FEED AND HARVEST FLOW THROUGH FILTER ASSEMBLY

CROSS-REFERENCE TO RELATED APPLICATIONS

This application is a filing under 35 U.S.C. 371 of international application number PCT/SE2012/050198, filed Feb. 22, 2012, published on Aug. 30, 2012 as WO 2012/115586, which claims priority to Swedish patent application number 1150158-2 filed Feb. 24, 2011.

FIELD OF THE INVENTION

The present invention generally relates to bioreactors comprising a perfusion filter and to a method for operating a bioreactor comprising a perfusion filter.

BACKGROUND OF THE INVENTION

Cell culture has generated considerable interest in recent years due to the revolution in genetic engineering and biotechnology. Cells are cultured to make for example proteins, receptors, vaccines, and antibodies for therapy, research, and for diagnostics.

It has long been recognized that perfusion culture offers relatively good economics for cell cultures. In this operation, cells are retained in the bioreactor, and the product is continuously removed along with toxic metabolic byproducts. Feed, containing nutrients, is added continually to the bioreactor. Perfusion culture operation is capable of achieving high cell densities and more importantly, the cells can be maintained in a highly productive state for weeks. This achieves much higher yields and reduces the size of the bioreactor necessary. It is also a useful technique for cultivating primary or other slow growing cells.

Perfusion operations have been greatly developed during recent years. U.S. Pat. No. 6,544,788 discloses a prior art bioreactor comprising a perfusion filter which allows liquid to be removed from the bioreactor without losing cells. The perfusion filter is constructed such that it is neutrally buoyant with respect to the culture media. It is placed inside the bioreactor so that it can move freely with bioreactor's rocking motion. The bottom surface of the filter consists of a liquid permeable, but cell-retentive membrane. A flexible tube allows the essentially cell-free filtrate to be drawn out from inside the filter. As the bioreactor is rocked, the filter moves rapidly back and forth in the culture media. This back and forth motion serves to clean the filter and allows it to operate without severe clogging. Nutrient feed is pumped into the bioreactor and the harvest filtrate is removed continuously, or at periodic intervals.

Even though the above-defined perfusion filter provides a satisfactory prevention of clogging of the filter, there is still a further desire to improve the prevention of clogging of the perfusion filter and extend the operational durability of the perfusion filter.

Documents U.S. Pat. No. 5,032,524, WO2007076865 and FR2679248 deal with the problems of clogging in filters in bioreactors. In each of the documents, a system including recirculation of liquid media is suggested. However, such systems are difficult to implement in bioreactors in which filter assembly is free to move within the chamber.

SUMMARY OF THE INVENTION

The objective of the present invention is to improve bioreactors of the above mentioned type so that the clogging prevention of a perfusion filter in a bioreactor is improved. A further objective is to extend the operational durability of the perfusion filter.

The objectives above are accomplished by the bioreactor according to the present invention which is defined in the pending claims.

According to the invention a bioreactor comprising a chamber capable of receiving a liquid media, and a filter assembly comprising a perfusion filter is provided. The filter assembly is disposed in the chamber and the filter assembly is free to move within the chamber. The filter assembly comprises means for coupling a harvesting flow through said filter and means for coupling a feed flow in an opposite direction compared to the harvesting flow through said filter.

The objectives above are also achieved by a method of operating a bioreactor comprising a chamber capable of receiving a liquid media, and a filter assembly comprising a perfusion filter, wherein the filter assembly is disposed in the chamber and the filter assembly is free to move within the chamber, wherein the method comprises removing a harvesting flow through said perfusion filter from the bioreactor and feeding a feed flow through said perfusion filter to the bioreactor. The harvesting flow is removed through said perfusion filter in an opposite direction compared to the feed flow.

Thereby it is possible to perform perfusion cell culture with an extended operational period due to the decreased clogging of the filter. The present invention provides an inexpensive cell culture bioreactor capable of perfusion operation without extensive clogging of the filter.

The means for coupling the flows may comprise a flexible tube attached to the filter assembly. The flexible tubes allow the movement of the perfusion filter inside the bioreactor in a desirable manner while they enable the flows to be fed or harvested in an effective way.

The filter assembly may comprise separate means for coupling the feed flow and the harvesting flow, respectively. To simplify the system and to keep feed and harvest flows out of contact with each other, the feed flow is pumped to the bioreactor by means of a feed pump and the harvesting flow is pumped from the bioreactor by means of a harvest pump. In this way, the mixing of the two flows is prevented. Therefore, it can be assured that the harvesting flow contains desirable cell-free products and the amount of nutrients in the harvesting flow is minimized. This is important since nutrients are often expensive and the amount of loss of nutrients should be minimized.

The filter assembly may comprise means for coupling the feed flow and harvesting flow in a coaxial manner. The feed flow may be arranged coaxially around the harvesting flow. Through this arrangement a possible turbulence is prevented. Also, through this arrangement, only a single coaxial tube connection is required which is less obstructive to the filter movement inside the bioreactor bag than arrangement with two separate tubes, i.e. the filter can move freely inside the bag.

The filter assembly may comprise at least two filters, whereby the filtration of the harvest liquid may be enhanced. The feed flow may then be directed to flow between the at least two filters. Through this arrangement the amount of feed liquid that can be caught inside the filter assembly may be minimized. Further, the turbulence may be prevented.

The method of operating the bioreactor may be carried out in a mode in which a specific volume of the harvesting flow is first removed from the bioreactor and then a substantially equal volume of the feed flow is fed to the bioreactor. In this way, the amount of the nutrients in the harvesting flow can be minimized. The removal of the harvesting flow and the feeding of the feed flow may be performed in periodic intervals.

Further aspects and advantages of the present invention will be apparent from the detailed description below and the figures illustrating examples of the ways to carry out the invention.

BRIEF DESCRIPTION OF THE DRAWINGS

For the purposes of illustrating the present invention a prior art construction of the bioreactor and preferred embodiments of the present invention are shown in the drawings, it being understood however, that the invention is not limited to the precise form shown by the drawings in which.

DETAILED DESCRIPTION OF THE INVENTION

The perfusion bioreactors based on wave-induced agitation include but are not limited to WAVE Bioreactor™ systems manufactured by GE Healthcare. Such bioreactors comprise a chamber, such as a plastic bag, that is partially filled with culture media and inflated to rigidity. The chamber, also herein referred to as a bioreactor bag, is placed on a rocking platform that moves it back and forth through a preset angle and at a preset rocking rate. The rocking motion induces waves in the culture media promoting agitation and oxygen transfer, both essential to good bioreactor performance.

The perfusion filter is constructed such that it is neutrally buoyant with respect to the culture media and it may be designed as for example shown by U.S. Pat. No. 6,544,788.

Figure 1:
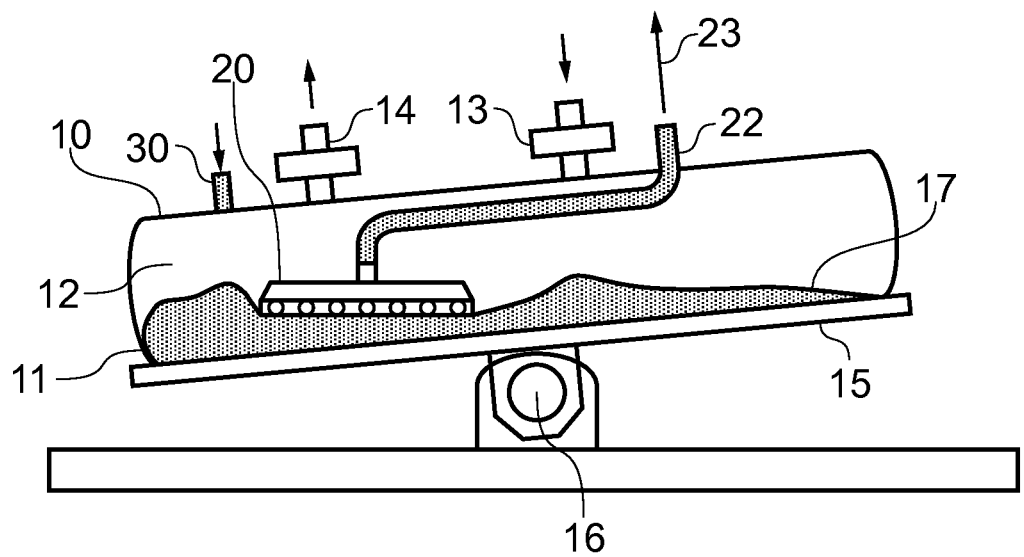
FIG. 1 is a cross-sectional view of a prior art perfusion bioreactor.

In FIG. 1 a prior art bioreactor is shown. The bioreactor comprises a plastic bag 10 that is partially (10% to 80%) filled with culture media and cells 11. The remainder of the chamber is inflated and consists of gas filled headspace 12. Oxygen, necessary for cell metabolism, is provided by air (or other oxygen enriched gas) introduced through sterilizing inlet filter 13. Exhaust air is vented from the chamber through exhaust filter 14. The bag 10 is attached to a rocking platform 15 that moves back and forth across pivot point 16. Typical rocking speed is 10 to 30 rocks per minute through an angle of 2 to 20 degrees from the horizontal plane. The perfusion filter 20 floats on the liquid surface 17. It can be seen from FIG. 1a that the lower surface of the filter 20 consists of a liquid permeable membrane 21 that is submerged. This membrane 21 has porosity such that cells cannot pass through it. The filter membrane 21 may be a sintered porous polyethylene sheet with a mean pore size of 7 microns (Porex T3). Other suitable plastics such as nylon and polyethylene could also be used. The filtration membrane 21 is heat welded to a non-porous upper layer 26. A hose barb port 27 is attached to the upper layer 26 so that the filtrate tube 22 may be easily attached. In this prior art solution, suction is applied on the flexible filtrate tube 22, cell-free filtrate 23 is drawn up into the filter 20 and removed from the bioreactor. The flexible tube 22 is the only attachment point of the filter 20. A polyethylene mesh 24 may be placed inside the filter 20 to prevent the filtration membrane 21 from being sucked flat against the upper layer 26 and choking off flow. The entire filter assembly 20 may be sealed by a thermally welded seam 25. Nutrients are fed to the bioreactor via a separate inlet port 30.

Figure 1A:
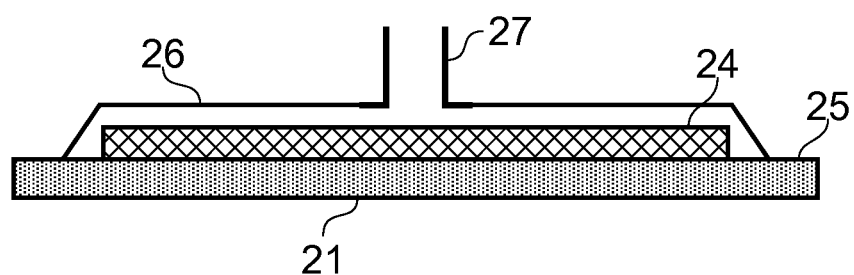
FIG. 1a is a cross-sectional view of the prior art filter assembly.
Figure 2:
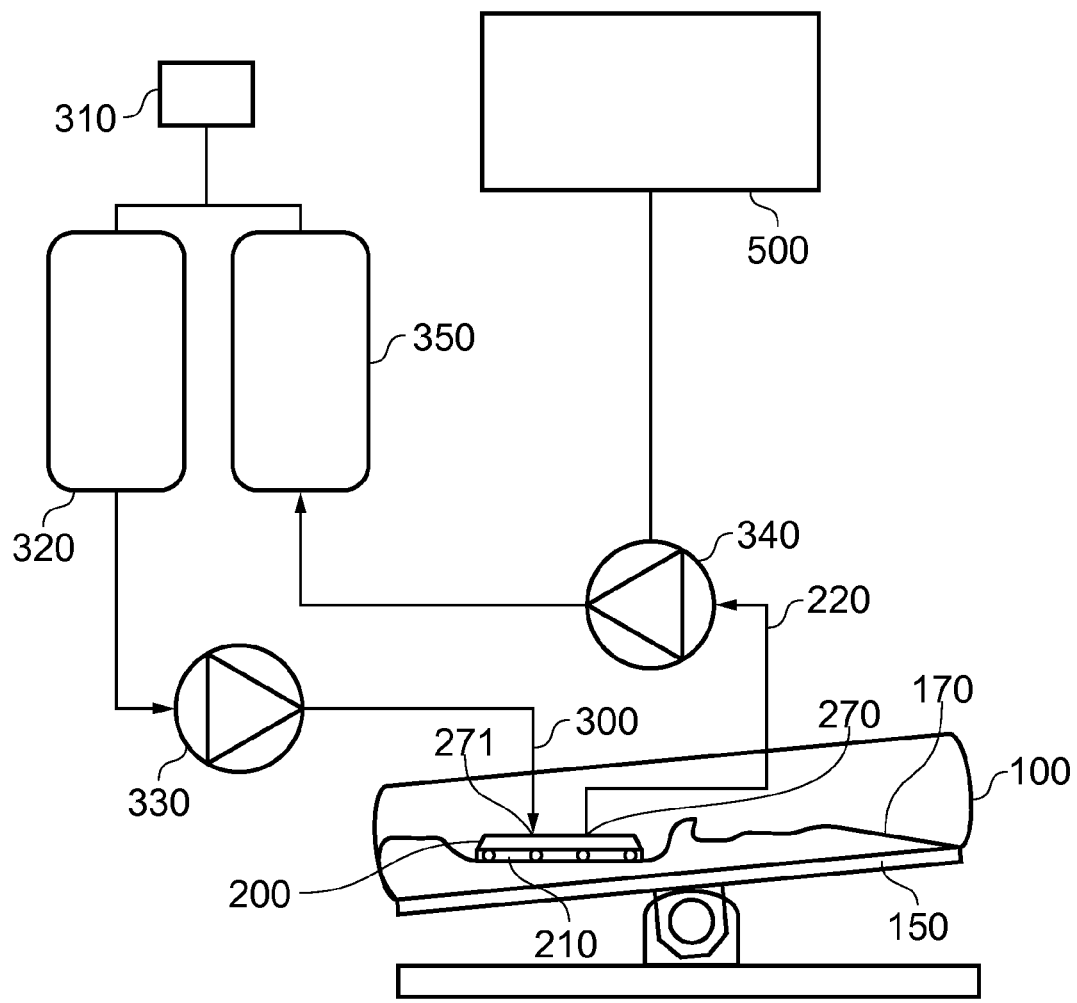
FIG. 2 is a schematic view of an embodiment of the bioreactor according to the present invention with flow control circuit.

In the present invention, as illustrated in FIG. 2, the perfusion filter 210 is comprised in a filter assembly 200 which further comprises means to couple a harvest flow tube 220, herein also called filtrate tube, and feed flow tube 300 to the filter assembly 200 such that the harvest flow and the feed flow comprising nutrients can flow through the perfusion filter 210 in opposite directions. The rocking platform 150, the bioreactor bag 100, the material for the flexible tubes 220, 300 and the type of the perfusion filter 210 may be similar or having corresponding features as discussed in connection with the prior art bioreactor above and as shown in FIGS. 1 and 1a.

The means to attach the flow tubes 220, 300 to the filter assembly may comprise for example hose barb ports to which the flexible tubes 220, 300 are connected. It is clear for the skilled person that any other suitable attachment means providing liquid and/ gas tight connection may be used.

The flexible tubes 220, 300 are coupled through the wall of the bioreactor bag 100. The flexible tubes 220, 300 are flexible enough to permit the filter assembly 200 to move freely on the liquid surface 170. If necessary, the length and the position of the flexible tubes 220, 300 in relation to the bioreactor wall may be arranged such that the movement of the perfusion filter assembly 200 is somewhat limited, e.g. to prevent the filter assembly 200 from colliding with the walls of the bioreactor 100. In such a way, the operational durability of the perfusion filter may be further increased.

The perfusion filter 200 and bioreactor bag 100 may be sterilized in situ by gamma radiation. In use the bag 100 is filled with growth promoting sterile nutrient media. Cells are added and the bag 100 is placed on the rocking platform 150. The bioreactor is rocked and aerated to promote cell growth.

The bioreactor according to the present invention may be operated as further illustrated in FIG. 2. The bioreactor is harvested, i.e. the harvesting flow (cell-free filtrate) is drawn up into the filter 210 and removed from the bioreactor by switching on the harvest pump 340. This pump sucks filtrate in a desired amount up through the perfusion filter 220 and pumps it into a collection vessel 350. The collection vessel is suspended by a hook which comprises means 310, such as a weight sensor, for measuring weight of the collection vessel 350. A controller 500 keeps the pump 340 on until preset and/or desired weight of harvest, as measured by gain of weight of the collection vessel 350, is delivered into the collection vessel 350. Next, the feed pump 330 is switched on. Nutrients are fed from a feed container 320 that is suspended from the same hook as the collection vessel 350. The rate of feed is controlled by feed pump 330. This feed pump 330 is operated intermittently by controller 500 pumping feed into the bioreactor bag 100 via a flexible tube 300 coupled to the filter assembly 200. The controller 500 turns the feed pump 330 on until preset weight of feed, as measured by loss in weight of the feed container 320, is delivered into the bioreactor bag 100. The amount of feed equals to the amount of harvest collected from the bioreactor bag 100. The cycle is then repeated. The frequency of cycling can be adjusted to give the desired overall perfusion rate. The cumulative amount of feed added and harvest removed can be easily calculated from the cycling of the weight sensor 310.

In another variant of the invention, the bioreactor bag 100 may be operated by first adding a feed flow of nutrients into the bioreactor bag 100 and then collecting the harvest. The control system 500 functions analogously with the one described above. When the feed is added first, the loss of weight in the feed container 320 is measured, and the amount of harvest is then adapted to be equal with the feed added to the reactor 100. Through this arrangement the level of nutrients can be kept relatively high during culturing.

In one variant of the invention, each of the feed container 320 and collection vessel 350 includes means for measuring weight, such as a weight sensor, respectively. In such an arrangement, the control system 500 is adapted to receive information from each sensor, respectively, and thereafter to adapt the amount of harvest and feed as equal. Through this arrangement the accuracy of the system may be further improved.

In a further embodiment of the invention, the weight measuring means, such as a weight sensor or a scale arrangement, is incorporated in the rocking platform 150 of the bioreactor. The control system functions 500 analogously with the one described above, i.e. the control system adapts the amount of harvest to be equal with the feed added to the reactor 100. Through such an arrangement the system may be constructed more compact.

In perfusion operation it is critical that cells not be allowed to leave the bioreactor. Otherwise, the cell concentration in the bioreactor will drop due to washout of the cells. In practice, a small amount of cell loss (<10%) is tolerated in order to remove dead and dying cells and to promote a low level of cell regrowth. Alarms can be programmed to warn of pump or filter failure to prevent the loss of valuable cells.

Figure 3:
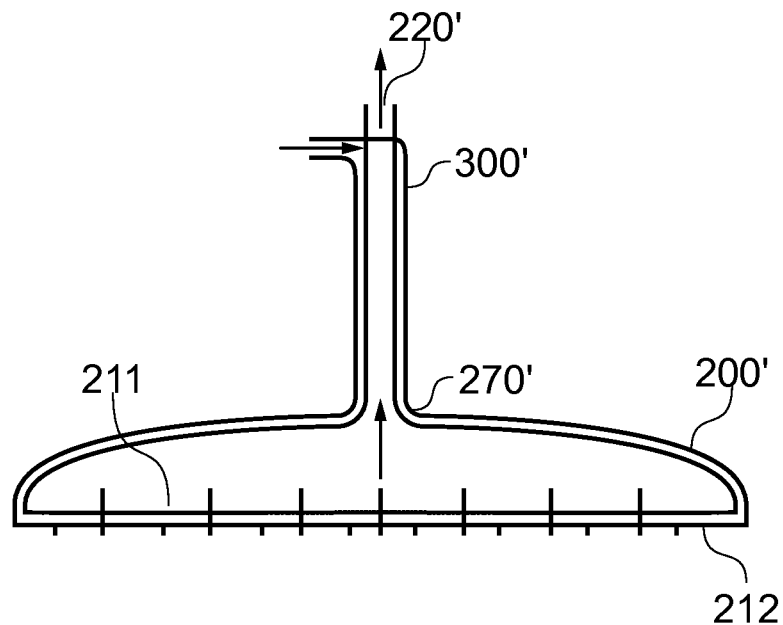
FIG. 3 is a schematic view of an embodiment of the perfusion filter assembly with a coaxial coupling for harvest flow and feed flow.

In FIG. 3 it is shown an embodiment in which the filter assembly 200' comprises coaxially arranged flexible tubing for the feed flow 300', and the harvesting flow 220'. The flexible tubes are coupled via a single coaxial coupling means 270' to the filter assembly 200', which coupling means may be of any suitable construction providing inlet for both the harvesting flow and the feed flow and attached to said filter assembly 200', and is not illustrated in more detail in the drawing. As illustrated in the FIG. 3, the feed flow 300' is arranged around the harvest flow 220' and directed to travel around the filter assembly 200' to the second perfusion filter 212. The harvesting flow 220' in connection with the removal of the filtrate travels through the both filters 211 and 212. Thereby, the harvesting flow 220' is removed from the bioreactor bag through the perfusion filter 212 in an opposite direction compared to the feed flow 300' and an enhanced filtration is obtained for the harvesting flow. Through this arrangement, it is possible to minimize the amount of feed flow that can be caught inside the filter assembly. Also, turbulence may be avoided. It is also possible to direct the feed flow and the harvest flow, which are arranged in a coaxial manner, through a single perfusion filter to the bioreactor bag, i.e. in a similar manner as illustrated in connection with FIG. 2.

In another variant (not illustrated in figures), the harvest flow tube and the feed flow tube may be attached side by side or at a close distance from each other on the filter assembly in a parallel manner. The feed flow may then be arranged to flow around the filter assembly and be fed to the bioreactor bag through a second perfusion filter in a similar manner as illustrated in connection with FIG. 3. The feed flow can also be arranged such that it flows through a single perfusion filter in a similar manner as illustrated in FIG. 2. By arranging the means for coupling the feed flow and harvest flow side by side and/or in a parallel manner, the free movement of the filter assembly inside the bioreactor can be ensured.

Figure 4:
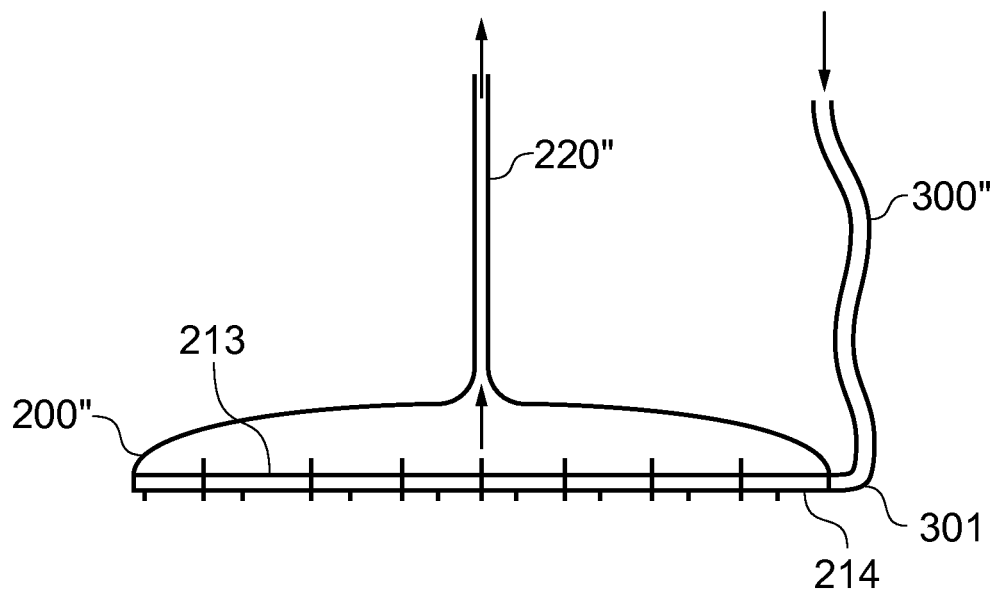
FIG. 4 is a schematic view of an embodiment of the perfusion filter assembly with a rim coupling for feed flow.

In FIG. 4 a further embodiment of the present invention is shown. The filter assembly 200" comprises two perfusion filters 213 and 214. The filter assembly 200" comprises flexible tube 300" for the feed flow and tube 220" for the harvesting flow. The feed flow tube 300" is attached to the rim of the filter assembly 200 and the feed flow is directed in between the two perfusion filters 213 and 214. Also through this arrangement, it is possible to minimize the amount of feed flow that can be caught inside the filter assembly. Also, turbulence may be avoided.

According to the present invention as defined above, the perfusion filter can be kept from clogging during an extended period due to the backflow provided on the perfusion filter surface. The clogging is prevented in an easy, economic and effective way.

Although the invention has been described in terms of specific embodiments and applications, persons skilled in the art, can in light of this teaching, generate additional embodiments without exceeding the scope or departing from the spirit of the claimed invention. The specific composition of the various elements of the perfusion bioreactor system, for example, should not be construed as a limiting factor. Accordingly, it is to be understood that the drawings and descriptions in this disclosure are proffered to facilitate comprehension of the invention and should not be construed to limit the scope thereof.

The invention claimed is:

1. A bioreactor comprising:
    a chamber capable of receiving a liquid media; and
    a filter assembly disposed in and free to move about the chamber;
    wherein the filter assembly is configured to:
    (i) receive a feed flow through a feed flow tube passing through a pathway formed between a first perfusion filter and a second perfusion filter of the filter assembly, the feed flow being pumped into the bioreactor by means of a feed pump; and
    (ii) produce a harvesting flow through the first and second perfusion filters and through a filtration tube in an opposite direction of the feed flow, the harvesting flow being pumped from the bioreactor by means of a harvest pump.

2. The bioreactor of claim 1, further comprising a flexible tube attached to the filter assembly, the flexible tube being configured to couple to the filter assembly.

3. The bioreactor of claim 1, wherein the filter assembly comprises means for coupling the feed flow and the harvesting flow, respectively.

4. The bioreactor of claim 1, wherein the filter assembly comprises means for coupling the feed flow and the harvesting flow in a coaxial manner.

5. The bioreactor of claim 4, wherein the feed flow is arranged coaxially around the harvesting flow.

6. The bioreactor of claim 1, wherein the filter assembly comprises at least two perfusion filters.

7. The bioreactor of claim 6, wherein the feed flow is directed to flow between the at least two perfusion filters.

8. A method of operating a bioreactor including a chamber capable of receiving a liquid media and a filter assembly disposed in and free to move about the chamber, the method comprising:

receiving a feed flow through a feed flow tube passing through a pathway formed between a first perfusion filter and a second perfusion filter of the filter assembly, the feed flow being pumped into the bioreactor by means of a feed pump; and producing a harvesting flow through the first and second perfusion filters and through a filtration tube in an opposite direction of the feed flow, the harvesting flow being pumped from the bioreactor by means of a harvest pump.

9. The method of claim 8, wherein the method further comprises:

first removing the harvesting flow from the bioreactor; and subsequently feeding to the bioreactor a volume of the feed flow substantially equal to a volume of the removed harvesting flow.

10. The method of claim 8, further comprising removing the harvesting flow and the feed flow in periodic intervals.

\* \* \* \* \*